(12) United States Patent
Barbour et al.

(10) Patent No.: US 9,304,285 B2
(45) Date of Patent: Apr. 5, 2016

(54) CATHETERIZATION AID FOR WOMEN

(71) Applicants: Edward Glenn Barbour, Raleigh, NC (US); Michael Eugene King, Holly Springs, NC (US)

(72) Inventors: Edward Glenn Barbour, Raleigh, NC (US); Michael Eugene King, Holly Springs, NC (US)

(*) Notice: Subject to any disclaimer, the term of this patent is extended or adjusted under 35 U.S.C. 154(b) by 0 days.

(21) Appl. No.: 14/469,868

(22) Filed: Aug. 27, 2014

(65) Prior Publication Data
US 2015/0062729 A1 Mar. 5, 2015

Related U.S. Application Data

(60) Provisional application No. 61/870,873, filed on Aug. 28, 2013.

(51) Int. Cl.
| G02B 7/182 | (2006.01) |
| F21V 33/00 | (2006.01) |
| A61M 25/01 | (2006.01) |
| A47G 1/16 | (2006.01) |
| F16M 1/00 | (2006.01) |

(52) U.S. Cl.
CPC *G02B 7/182* (2013.01); *A47G 1/16* (2013.01); *A61M 25/01* (2013.01); *F16M 1/00* (2013.01); *A61M 2209/084* (2013.01); *F21V 33/004* (2013.01)

(58) Field of Classification Search
CPC ..... G02B 7/182; F21V 33/004; A61M 25/01; A47G 1/16
USPC ................. 359/872, 875, 880, 881, 882, 900; 362/139, 142, 144; 248/471, 472, 474, 248/479, 481
See application file for complete search history.

(56) References Cited

U.S. PATENT DOCUMENTS

| 2,017,472 | A | * | 10/1935 | Re | A47G 1/02 248/474 |
| 4,004,850 | A | * | 1/1977 | Nelson | A01M 31/00 248/166 |
| 4,771,300 | A | * | 9/1988 | Bryan | G03B 15/06 359/839 |
| 4,850,688 | A | * | 7/1989 | Rosenberg | A45D 42/18 359/860 |
| 4,966,450 | A | * | 10/1990 | Mori | A61N 5/06 248/474 |
| 5,210,656 | A | * | 5/1993 | Williamson | G03B 15/06 248/474 |
| 5,311,366 | A | * | 5/1994 | Gerace | A61B 5/0079 248/476 |
| 5,359,461 | A | * | 10/1994 | Rice | A45D 20/12 248/469 |
| 5,556,070 | A | * | 9/1996 | Viebrock | E01F 9/016 248/188.5 |
| 6,273,575 | B1 | * | 8/2001 | Downs | A61B 1/307 359/871 |
| 6,382,802 | B1 | * | 5/2002 | Goodman | A45D 42/16 248/469 |
| 7,165,860 | B1 | * | 1/2007 | Metzger | A47G 1/24 362/143 |
| 8,506,099 | B1 | * | 8/2013 | Abdool | A47G 1/24 248/469 |

* cited by examiner

*Primary Examiner* — Ricky D Shafer
(74) *Attorney, Agent, or Firm* — Coats and Bennett PLLC

(57) ABSTRACT

A self-catheterization aid for a woman that comprises a tripod. Mounted to the tripod is a mirror that can be moved and adjusted in various planes. Mounted to the mirror is a battery-powered light. The device enables a woman to appropriately position the self-catheterization device such that the mirror and light is aimed at the urethra area. This enables the woman to clearly see the inlet to the urethra which in turn facilitates self-catheterization.

11 Claims, 3 Drawing Sheets

CATHETERIZATION AID FOR WOMEN

This application claims priority under 35 U.S.C. §119(e) from the following U.S. provisional application: Application Ser. No. 61/870,873 filed on Aug. 28, 2013. That application is incorporated in its entirety by reference herein.

FIELD OF THE INVENTION

The present invention relates to medical devices, and more particularly to a device that assists a woman in performing self-catheterization.

BACKGROUND OF THE INVENTION

A person's bladder functions to collect and hold urine, and from time-to-time, the bladder functions to evacuate the urine. Some people have a condition that is sometimes referred to as urinary retention. This simply means that the bladder is unable to evacuate urine.

There are a number of treatments for urinary retention. One approach or solution to this problem involves intermittent self-catheterization where, in the case of a woman, the woman catheterizes herself periodically. This is generally recognized as a safe and effective way for women to deal with urinary retention.

There is one problem with self-catheterization involving a female. Because of the anatomical position of the inlet opening of the female urethra, it is difficult for a woman to self-catheterize herself.

There has been and continues to be attempts at designing aids for assisting women with self-catheterization. For the most part, the approaches of the prior art have fallen short for one reason or another. For example, it is known to provide a vaginal insert that has an associated catheterization guide. To use this device, the woman inserts the device into her vagina with the idea that the associated guide will align with her urethra. In many cases, the guide will not properly align with the woman's urethra and, hence, the device is of little or no use and only leads to frustration.

Therefore, there has been and continues to be a need for a simple and easy-to-use catheterization aid for females that will enable a female to easily and quickly execute self-catheterization.

SUMMARY OF THE INVENTION

The present invention entails a self-catheterization aid for a woman that comprises a support that, in one embodiment, is a tripod. Mounted to the support or tripod is a mirror that can be moved and adjusted in various planes. Mounted to the mirror is a battery-powered light. This device enables a woman to appropriately position the self-catheterization aid or device such that the mirror and light are aimed at the vaginal area, including the urethra area, resulting in the area being visible to the woman via the mirror. This enables the woman to clearly see the inlet to the urethra, which in turn facilitates self-catheterization.

In one embodiment, the present invention includes a self-catheterization aid for a woman which includes an adjustable tripod with a series of legs and a top. A sleeve is mounted to the top of the tripod and the shaft is supported within the sleeve and includes an axis. A carrier is connected to the shaft and rotatable about the axis of the shaft. A handle projects from the carrier for manipulating the carrier. The carrier includes an adjustable mirror mount that is pivotally connected on the carrier. A mirror is mounted to the mirror mount. An electric powered light is mount to the mirror. The mirror and light can be adjusted by actuating the handle and moving the carrier or by adjusting the mirror mount relative to the carrier.

In another embodiment, there is provided a method of assisting a woman in inserting a catheter into the urethra of the woman. This method includes positioning a self-catheterization aid such that the self-catheterization aid is aligned with a urethra area of a woman. The method further includes adjusting the position of a mirror forming a part of the self-catheterization aid such that the urethra area is reflected in the mirror. Further, the method includes directing a beam of light from the self-catheterization aid onto the urethra area and forming a reflection of the urethra area in the mirror. Further, the method includes guiding a catheter into the urethra wherein the reflection of the urethra area in the mirror assists the woman in executing self-catheterization.

In another embodiment, the present invention includes a self-catheterization aid for assisting a woman in inserting a catheter into her urethra. The self-catheterization aid comprises an adjustable support having an upper portion and a plurality of legs extending from the upper portion wherein each leg is moveable back and forth between an inner collapsed position and an outer expanded position. The self-catheterization aid includes a carrier mounted above the upper portion of the adjustable support wherein the carrier is movably mounted relative to the adjustable support. The carrier further includes a mirror mount. In addition, there is a mirror mounted to the mirror mount. A light is mounted to the mirror for directing a light beam away from the mirror and onto the urethra area of the woman.

Other objects and advantages of the present invention will become apparent and obvious from a study of the following description and the accompanying drawings which are merely illustrative of such invention.

DESCRIPTION OF EXEMPLARY EMBODIMENT

Figure 1:
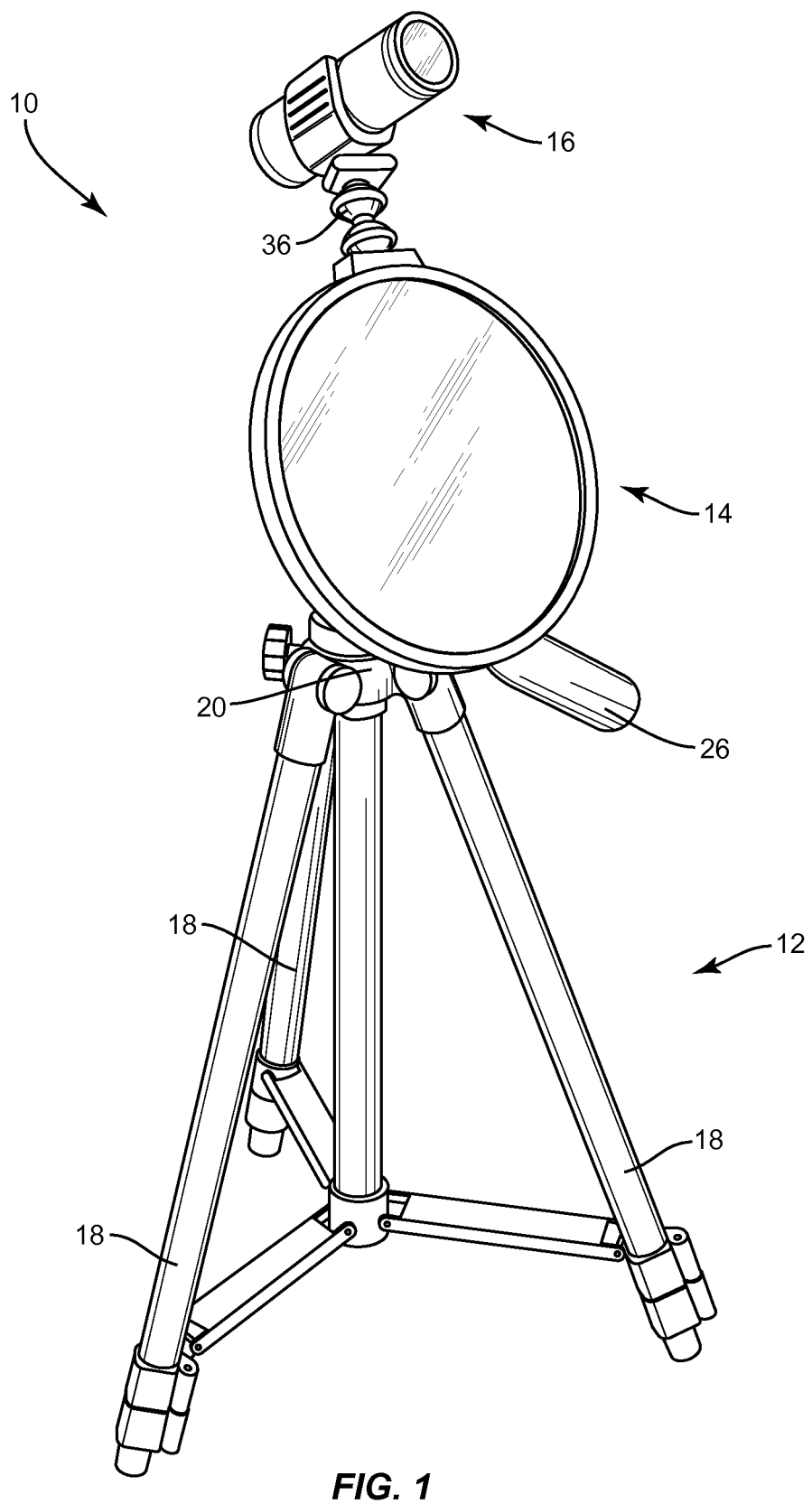
FIG. 1 is a perspective view of the self-catheterization aid of the present invention.

With further reference to the drawings, the self-catheterization aid is shown therein and indicated generally by the numeral 10. As will be appreciated from viewing the drawings, the self-catheterization aid or device 10 comprises three basic components: a support structure 12, a mirror 14, and a light 16. As seen in the drawings, the mirror 14 is mounted to the support structure 12 and the light, in turn, is mounted to the mirror.

The support structure 12 can vary in design. More particularly, the support structure 12 can assume various forms which can support the mirror 14 and light 16. Support structure 12 should be stable when positioned on a support. Its height preferably should be adjustable. Further, the support structure 12, in a preferred embodiment, should be lightweight, compact and easy to carry. Preferably, the design of the self-catheterization aid 10 is such that it can be packaged and carried by the woman in an inconspicuous manner. The support structure 12 can be collapsed such that the structure as a whole can be transformed into a compact design that can be contained within a small carrying bag or case. Finally, the support structure 12 should be easy to handle and manipulate.

One design for the support structure 12 is in the form of a tripod. The tripod design is shown in the accompanying drawings. The tripod includes a series of legs 18. Each leg may be telescoping such that the entire device 10 can be adjusted for height. Each leg 18 is connected at an upper end to a top connector or plate 20. Legs 18 are mounted to the underside of a top connector 20 such that the legs can be moved inwardly and outwardly. Support structure 12 with the inwardly and outwardly moving legs 18 can be positioned in a compact configuration by moving the legs 18 inwardly to where the legs lie directly adjacent each other. This enables the catheterization aid to be packaged in a flexible bag and wherein the bag can, in turn, be placed in a purse carried by the woman.

Figure 2:
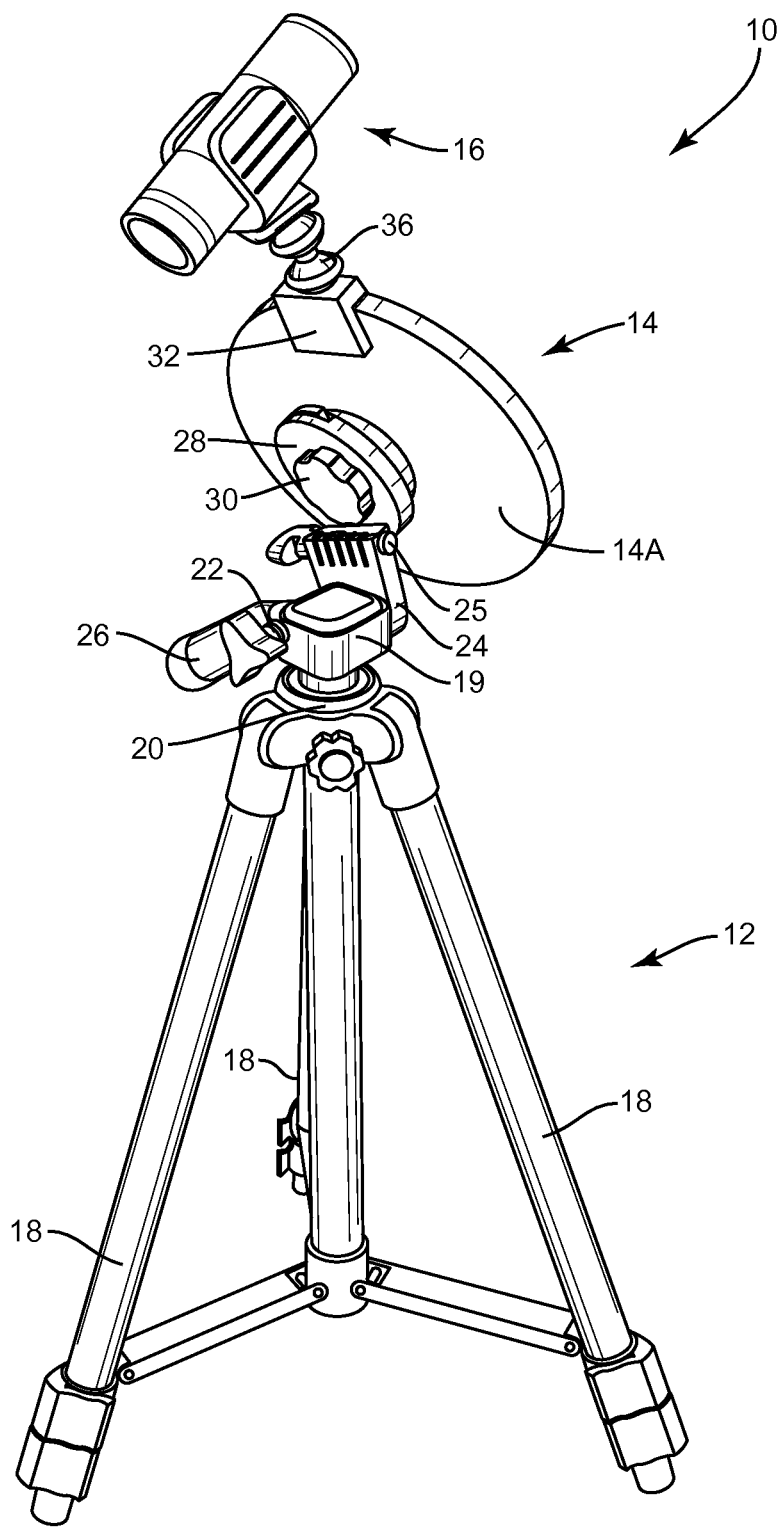
FIG. 2 is another perspective view of the self-catheterization aid viewed from a different angle.
Figure 3:
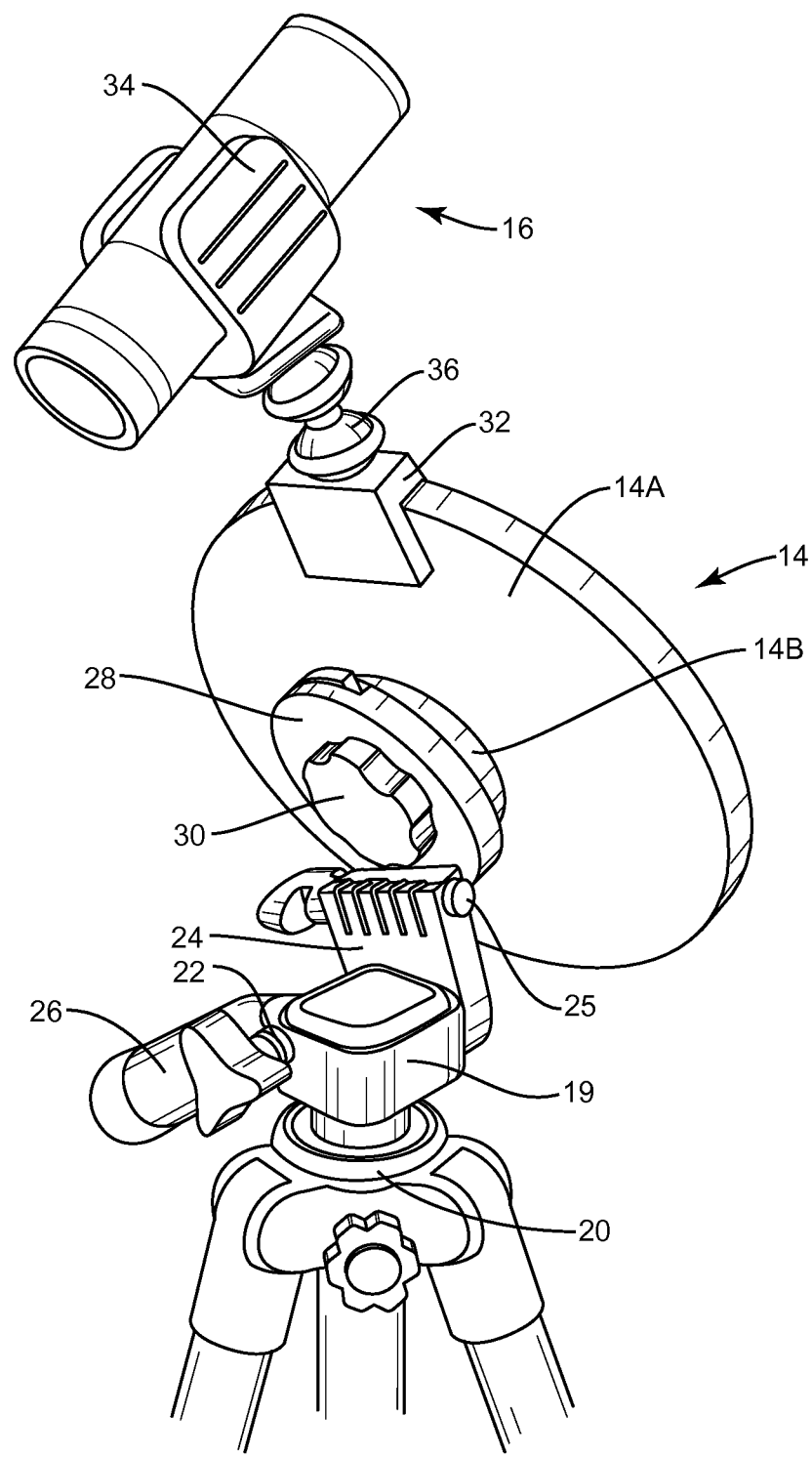
FIG. 3 is a fragmentary perspective view showing a top portion of the self-catheterization aid.

Mounted to the top connector 20 is a sleeve or block s19. A shaft 22 is rotatable in the block 19. A carrier 24 is rotatably mounted on the shaft 22. Projecting from the carrier 24 is a handle 26. As seen in the FIGS. 2 and 3, the carrier 24 includes a bifurcated portion. A pivot pin 25 is connected across the bifurcated portion of the carrier 24. A mirror mount 28 is pivotally connected on the pivot pin 25 on the carrier 24. The mirror 14 is mounted to the mirror mount 28. In particular, mirror 14 includes a back face 14A. Formed on the back face 14A of the mirror is a center boss 14B. Center boss 14B is threaded. There is provided a thumbscrew 30 that projects through an opening in the carrier 24 and screws into the threaded center boss 14B. That is how the mirror is supported on the support structure 12.

It will be appreciated by those skilled in the art that there are various ways of supporting the mirror 14. In lieu of the mirror mount 28 and thumb screw 30 shown in the drawings, there could be provided a quick attach-detach mechanism for connecting the carrier 24 to the mirror 14. Various quick attach and detach mechanisms can be used.

There is provided an L-shaped mounting bracket 32 that is mounted to the back face 14A of the mirror 14. A ball mount 36 is secured to a portion of the L-shaped bracket 32. A cradle 34 is secured on the ball mount 36. As seen in the drawings, the light 16, which is a battery-powered light, is elongated and seats in the cradle 34. In one embodiment, the light 16 includes a central area that is designed to frictionally fit in the cradle 34.

By moving the handle 26, the mirror 14 and light 16 can be articulated back and forth. That is, the mirror 14 and the light 16 can be moved and adjusted by rotating the support shaft 22 within block 19. Besides rotating about the axis, both the mirror 14 and light 16 can rotate about the pivot pin 25 provided in the carrier 24. This, of course, enables the mirror 14 and the light 16 to rotate about two separate axes and greatly facilitates the adjustment of the device when being used for self-catheterization. There is also a substantial adjustment provided for the light 16. The ball mount 36 enables the light 16 to be rotated about an infinite number of axes on the upper portion of the ball mount.

In use, the device 10 of the present invention is utilized by a woman to assist her in properly inserting a catheter into her urethra. Thus, the device 10 is positioned with respect to the woman such that the area around the urethra is reflected by the mirror 14 in such a fashion that the area around the urethra can easily be seen. Further, in order to facilitate self-catheterization, the battery-powered light is turned on and adjusted so as to direct a light beam onto the area around the opening to the urethra. This beam of light creates a clear reflection of the urethra area in the mirror 14 and enables the woman to see clearly the inlet to her urethra and to manipulate the catheter.

As seen in the drawings, the device 10 is relatively small and compact and can be easily packaged in a small flexible bag and carried on the person. In some cases, it may be desirable to provide a larger support structure for use in the home.

The device of the present invention is especially useful to a woman when she begins to employ self-catheterization. Over a period of time, with the assistance of the device of the present invention, a person will become more adept at self-catheterization and eventually may not need the aid that is provided by the present invention. That is, it is possible that, after repeated self-catheterizations, a person will be able to achieve such simply because of repeated catheterization exercises.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A self-catheterization aid for a woman comprising:
   an adjustable tripod with a series of legs and a top;
   a sleeve mounted to the top of the tripod;
   a shaft supported in the sleeve and including an axis;
   a carrier connected to the shaft and rotatable about the axis of the shaft;
   a handle projecting from the carrier for manipulating the carrier;
   wherein the carrier includes an adjustable mirror mount that is pivotally connected on the carrier;
   a mirror mounted to the mirror mount;
   an electric powered light mounted to the mirror;
   wherein the mirror and light can be adjusted by actuating the handle and moving the carrier or by adjusting the mirror mount relative to the carrier; and
   wherein the mirror mount is pivotally connected to the carrier via a pivot pin.

2. The self-catheterization aid of claim 1 wherein the mirror includes a back face, a threaded boss secured on the back face of the mirror; and wherein there is provided a threaded screw that projects from the carrier and is threaded into the threaded boss.

3. The self-catheterization aid of claim 2 wherein the threaded screw includes a thumb screw that projects through a portion of the carrier into the threaded boss.

4. The self-catheterization aid of claim 1 further including a bracket secured to the mirror; a ball joint secured to the bracket; a cradle secured to the ball joint; and wherein the electric power light is secured within the cradle.

5. A self-catheterization aid for assisting a woman in inserting a catheter into her urethra, the self-catheterization aid comprising:
   an adjustable support having an upper portion and a plurality of legs extending from the upper portion and wherein each leg is moveable back and forth between an inner collapsed position and an outer expanded position;
   a carrier mounted above the upper portion of the adjustable support wherein the carrier is movably mounted relative to the adjustable support;
   the carrier including a mirror mount;
   a mirror mounted to the mirror mount;
   a light mounted to the mirror for directing a light beam away from the mirror;

wherein the carrier is bifurcated and includes a main portion and the mirror mount and wherein the mirror mount is pivotally mounted to the main portion via a pivot axis; and wherein the mirror includes a back face having a threaded boss and wherein the mirror mount of the carrier includes a thumb screw that is threaded into the boss so as to secure the mirror to the carrier.

6. The self-catheterization aid of claim 5 including a U-shaped cradle for receiving and holding the light and wherein the cradle is supported on the mirror.

7. The self-catheterization aid of claim 6 wherein there is provided at least one ball joint operatively interconnected between the mirror and the cradle for enabling the cradle and the light held thereby to be adjusted relative to the mirror.

8. The self-catheterization aid of claim 7 wherein the ball joint is supported on an L-shaped bracket secured to the back side of the mirror.

9. The self-catheterization aid of claim 5 including a sleeve secured to the upper portion of the adjustable support; and a shaft contained within the sleeve and wherein the carrier is secured to the shaft.

10. The self-catheterization aid of claim 5 wherein the adjustable support includes a tripod including three legs with each leg extending from the upper portion and being secured into the upper portion of the tripod such that the legs can move back and forth between the collapsed and expanded positions.

11. A self-catheterization aid for a woman comprising:
an adjustable tripod with a series of legs and a top;
a sleeve mounted to the top of the tripod;
a shaft supported in the sleeve and including an axis;
a carrier connected to the shaft and rotatable about the axis of the shaft;
a handle projecting from the carrier for manipulating the carrier;
wherein the carrier includes an adjustable mirror mount that is pivotally connected on the carrier;
a mirror mounted to the mirror mount;
an electric powered light mounted to the mirror;
wherein the mirror and light can be adjusted by actuating the handle and moving the carrier or by adjusting the mirror mount relative to the carrier; and
wherein the mirror includes a back face, a threaded boss secured on the back face of the mirror; and wherein there is provided a threaded screw that projects from the carrier and is threaded into the threaded boss.

* * * * *